(12) United States Patent
Ito et al.

(10) Patent No.: US 10,844,347 B2
(45) Date of Patent: Nov. 24, 2020

(54) METHOD FOR PRODUCING DRIED MICROBIAL CELLS

(71) Applicant: Kabushiki Kaisha Yakult Honsha, Minato-ku (JP)

(72) Inventors: Masahiko Ito, Tokyo (JP); Kisaku Shimura, Tokyo (JP); Satoru Shirota, Tokyo (JP); Keiko Kasaha, Tokyo (JP); Yasuhiro Moteki, Tokyo (JP); Akihisa Matsui, Tokyo (JP); Satoshi Miida, Tokyo (JP)

(73) Assignee: Kabushiki Kaisha Yakult Honsha, Minato-ku (JP)

( * ) Notice: Subject to any disclaimer, the term of this patent is extended or adjusted under 35 U.S.C. 154(b) by 186 days.

(21) Appl. No.: 15/771,728

(22) PCT Filed: Oct. 28, 2016

(86) PCT No.: PCT/JP2016/082125
§ 371 (c)(1),
(2) Date: Apr. 27, 2018

(87) PCT Pub. No.: WO2017/073752
PCT Pub. Date: May 4, 2017

(65) Prior Publication Data
US 2019/0062693 A1  Feb. 28, 2019

(30) Foreign Application Priority Data

Oct. 30, 2015 (JP) .................. 2015-214299

(51) Int. Cl.
*C12N 1/04* (2006.01)
*C12N 1/20* (2006.01)
*A23L 33/135* (2016.01)

(52) U.S. Cl.
CPC .............. *C12N 1/04* (2013.01); *A23L 33/135* (2016.08); *C12N 1/20* (2013.01); *A23V 2002/00* (2013.01); *A23Y 2220/17* (2013.01)

(58) Field of Classification Search
CPC combination set(s) only.
See application file for complete search history.

(56) References Cited

U.S. PATENT DOCUMENTS 9,504,275 B2 * 11/2016 Harel ................ A23P 10/30

FOREIGN PATENT DOCUMENTS

| EP | 1 281 752 A1 | 2/2003 |
| JP | 58-107181 A | 6/1983 |
| JP | 3504365 B2 | 3/2004 |
| JP | 2010-4787 A | 1/2010 |
| WO | WO 2012/021783 A2 | 2/2012 |

OTHER PUBLICATIONS

Extended European Search Report dated May 14, 2019 in corresponding European Patent Application No. 16859980.1, 6 pages.
E.P.W. Kets et al., "Citrate Increases Glass Transition Temperature of Vitrified Sucrose Preparations", Cryobiology, vol. 48, No. 1, XP055585587, Feb. 1, 2004, pp. 46-54.
International Search Report dated Jan. 24, 2017 in PCT/JP2016/082125 filed Oct. 28, 2016.
De Antoni, G. L., et al., "Trehalose, a Cryoprotectant for *Lactobacillus bulgaricus*", Cryobiology, 1989, vol. 26, pp. 149-153.

* cited by examiner

*Primary Examiner* — Heidi Reese
(74) *Attorney, Agent, or Firm* — Oblon, McClelland, Maier & Neustadt, L.L.P.

(57) ABSTRACT

An object is to provide a method for producing dried microbial cells with a high viable cell survival rate after long-term storage at a high temperature. A method for producing dried microbial cells that achieves the above-mentioned object is characterized in that microbial cells are suspended in a dispersion medium containing a protective agent, an antioxidant, and a chelating agent, followed by drying.

6 Claims, No Drawings

METHOD FOR PRODUCING DRIED MICROBIAL CELLS

TECHNICAL FIELD

The present invention relates to a method for producing dried microbial cells, more particularly relates to a method for producing dried microbial cells with a high viable cell survival rate after long-term storage at a high temperature.

BACKGROUND ART

Lactic acid bacteria known as enteric bacteria have been widely used conventionally in the production of dairy products such as yogurt and cheese, and further, the development of foods, drinks, etc. using dried lactic acid bacteria has been advanced recently. Then, in order to obtain the effect of lactic acid bacteria, it is desired to utilize microbial cells alive, however, in a step of obtaining dried microbial cells, the microbial cells are often damaged and killed, and it was difficult to obtain a necessary amount of viable cells.

Then, it is known that in order to reduce the damage or killing of microbial cells, a component contained in a dispersion medium to be used when drying the microbial cells is important, and for example, the addition of sodium glutamate (PTL 1) or trehalose (NPL 1) to a dispersion medium, or the use of these components in combination (PTL 2) are disclosed.

On the other hand, when considering the aspect of distribution of dried microbial cells, the dried cells whose survival rate is maintained high even if the cells are stored at normal temperature (20 to 40° C.) for a long period of time have been demanded. It is generally considered that as the temperature is higher, the deterioration of a product during storage is accelerated within a normal temperature range, and in particular, the quality stability at a high temperature (30 to 40° C.) is important.

CITATION LIST

Patent Literature

PTL 1: Japanese Patent No. 3504365
PTL 2: JP-A-2010-4787

Non Patent Literature

NPL 1: G. L. DE ANTONI et al., "Trehalose, a Cryoprotectant for *Lactobacillus bulgaricus*" Cryobiology 26, pp. 149-153, 1989

SUMMARY OF INVENTION

Technical Problem

Accordingly, an object of the present invention is to provide a method for producing dried microbial cells with a high viable cell survival rate after long-term storage at a high temperature.

Solution to Problem

The present inventors conducted intensive studies in order to achieve the above-mentioned object, and as a result, they found that the viable cell survival rate after long-term storage at a high temperature is increased by previously suspending microbial cells in a dispersion medium containing a protective agent, an antioxidant, and a chelating agent in combination before drying the microbial cells, followed by drying, and thus completed the present invention.

That is, the present invention is a method for producing dried microbial cells characterized in that microbial cells are suspended in a dispersion medium containing a protective agent, an antioxidant, and a chelating agent, followed by drying.

Further, the present invention is dried microbial cells, which are obtained by drying microbial cells using a dispersion medium containing a protective agent, an antioxidant, and a chelating agent.

Further, the present invention is a dispersion medium for drying microbial cells, containing a protective agent, an antioxidant, and a chelating agent.

Advantageous Effects of Invention

According to the method of the present invention, dried microbial cells with a high viable cell survival rate are obtained even if the cells are stored at a high temperature for a long period of time. Therefore, the dried microbial cells obtained by the method of the present invention are extremely excellent from the viewpoints of distribution and storage.

DESCRIPTION OF EMBODIMENTS

A microorganism for which dried microbial cells are obtained by the method of the present invention is not particularly limited, however, examples thereof include *Lactobacillus* bacteria such as *Lactobacillus casei*, *Lactobacillus gasseri*, *Lactobacillus acidophilus*, *Lactobacillus cremoris*, *Lactobacillus helveticus*, *Lactobacillus salivarius*, *Lactobacillus fermentum*, *Lactobacillus yoghurti*, *Lactobacillus delbrueckii* subsp. *bulgaricus*, *Lactobacillus delbrueckii* subsp. *delbrueckii*, *Lactobacillus johnsonii*, and *Lactobacillus mali*, *Bifidobacterium* bacteria such as *Bifidobacterium bifidum*, *Bifidobacterium breve* and *Bifidobacterium longum*, *Streptococcus* bacteria such as *Streptococcus thermophilus* and *Streptococcus lactis*, *Lactococcus* bacteria such as *Lactococcus lactis* subsp. *lactis*, *Lactococcus lactis* subsp. *cremoris*, *Lactococcus plantarum*, and *Lactococcus raffinolactis*, and *Enterococcus* bacteria such as *Enterococcus faecalis* and *Enterococcus faecium*, and among these, one species or two or more species can be used. Preferred examples thereof include *Lactobacillus* bacteria, and *Lactobacillus casei* is more preferred, and *Lactobacillus casei* YIT 9029 (FERM BP-1366, date of deposit: May 1, 1981, the International Patent Organism Depositary, the National Institute of Technology and Evaluation (#120, 2-5-8 Kazusakamatari, Kisarazu-shi, Chiba-ken, 292-0818, Japan) is particularly preferred.

In the implementation of the method of the present invention, first, a microorganism is cultured according to a conventional method, and subsequently, the cells are collected using, for example, a DeLaval centrifuge or the like, and then washed as needed.

The thus collected microbial cells are added into a dispersion medium which is an aqueous solution containing a protective agent, an antioxidant, and a chelating agent (hereinafter, also simply referred to as "dispersion medium of the present invention") and suspended therein, and the resulting suspension is dried, whereby target dried microbial cells can be obtained. A solvent of the dispersion medium is not particularly limited, however, for example, drinkable water such as purified water or deionized water can be used. The dispersion medium of the present invention is a dispersion medium for drying microbial cells and contains a protective agent, an antioxidant, and a chelating agent.

Further, a dispersion medium composed of a protective agent, an antioxidant, and a chelating agent is preferred.

The protective agent to be used in the dispersion medium of the present invention is not particularly limited, however, for example, glutamic acid or a salt thereof, a disaccharide, glycerol, maltodextrin, cyclodextrin, powdered skim milk, or the like can be used, and it is preferred to use glutamic acid or a salt thereof and/or a disaccharide, and examples of the glutamate salt include sodium glutamate and potassium glutamate, and particularly, sodium glutamate is preferred. Examples of the disaccharide include trehalose, sucrose, lactose, and maltose, and trehalose is preferred. Further, sodium glutamate and/or a disaccharide are/is preferred, and sodium glutamate and/or trehalose are/is more preferred. The content of the protective agent in the dispersion medium of the present invention is preferably from 1 to 40 mass % (hereinafter denoted by %), more preferably from 5 to 30%.

Further, the antioxidant to be used in the dispersion medium of the present invention is not particularly limited, however, for example, ascorbic acid or a salt thereof, vitamin E, catechin, glutathione, astaxanthin, or the like can be used, and example of the ascorbate salt include sodium ascorbate and calcium ascorbate, and particularly, sodium ascorbate is preferred. The content of the antioxidant in the dispersion medium of the present invention is preferably from 0.01 to 10%, more preferably from 0.05 to 5%.

Further, the chelating agent to be used in the dispersion medium of the present invention is not particularly limited, however, for example, ethylenediaminetetraacetic acid (EDTA), citric acid or a salt thereof, phytic acid, or the like can be used. Examples of the citrate salt among these include sodium citrate. The content of the chelating agent in the dispersion medium of the present invention is preferably from 0.1 to 10%, more preferably from 0.5 to 5%.

Further, it is preferred to use an aqueous solution containing sodium glutamate, trehalose, sodium ascorbate, and sodium citrate as the dispersion medium of the present invention.

The microbial cell count in a cell suspension in which microbial cells are suspended in the dispersion medium of the present invention is from about $1.0 \times 10^5$ to $4.0 \times 10^{14}$ cfu/mL, more preferably from $1.0 \times 10^7$ to $4.0 \times 10^{13}$ cfu/mL.

The drying in the method of the present invention is not particularly limited, and for example, a known drying method such as lyophilization or spray drying can be utilized, however, in order to increase the microbial survival rate in the drying step, lyophilization is preferred. Examples of the drying conditions in the lyophilization method include conditions in which a freezing treatment at $-35°$ C. to $-45°$ C. for 6 to 12 hours is performed, and thereafter a drying treatment at $12°$ C. to $32°$ C. for 40 to 90 hours is performed. Examples of a lyophilizer include TAKARA FREEZE-DRYER TF20-80 TANNS (TAKARA ATM Ltd.).

The thus obtained dried microbial cells (hereinafter also referred to as "dried microbial cells of the present invention") have a high viable cell survival rate after long-term storage at a high temperature as shown in the below-mentioned examples, and specifically, in a case where the dried microbial cells are ground using a mill, and the ground cells are filled in capsules (made of hydroxypropylmethyl cellulose) in an amount of 0.2 g per capsule under a general atmospheric composition without degassing, and then, the capsules are placed in an aluminum pouch along with an oxygen absorber (manufactured by Mitsubishi Gas Chemical Company, Inc.) and stored at $35°$ C. for 4 weeks, the ratio of the viable cell count after storage to the viable cell count at the start of storage (survival rate) is 30% or more. Further, in a case where the dried microbial cells are ground using a mill, and the ground cells are filled in capsules (made of hydroxypropylmethyl cellulose) in an amount of 0.2 g per capsule under a general atmospheric composition without degassing, and then, the capsules are placed in an aluminum pouch along with an oxygen absorber (manufactured by Mitsubishi Gas Chemical Company, Inc.) and stored under a series of conditions of $2°$ C. for 1 day, $35°$ C. for 2 days, $30°$ C. for 6 days, and $22°$ C. for 6 months as storage conditions in which the temperature is changed during storage, the survival rate is 40% or more.

The dried microbial cells of the present invention do not have a large strength immediately after lyophilization, and therefore have an effect that the cells can be easily ground thereafter. Further, the dried microbial cells have favorable dispersibility when the cells are suspended in water, and therefore, lyophilization is completed in a short time. Further, the dried microbial cells have low hygroscopicity, and therefore do not form an aggregate even after a long-term storage, and the handleability is favorable, and also the appearance, color, smell, etc. are the same as those at the start of storage and favorable.

Further, the dried microbial cells of the present invention are dried microbial cells obtained by drying microbial cells using a dispersion medium containing a protective agent, an antioxidant, and a chelating agent. The dried microbial cells can be utilized in foods and drinks directly or by mixing with another food material to be generally added to foods. Examples of the foods include meat processed foods such as ham and sausages, processed fishery foods such as Kamaboko (boiled fish paste loaf) and Chikuwa (tube-shaped boiled fish paste cake), bread, confectionery, butter, and fermented milk such as yogurt, and examples of the drinks include soft drinks, dairy lactic acid bacteria drinks, and lactic acid bacteria drinks. Further, examples of the forms of foods and drinks include generally used forms of foods and drinks, for example, solids such as powders and granules, pastes, liquids, and the like. Further, the dried microbial cells may be processed into tablets, powders, chewable tablets, hard capsules, soft capsules, pills, and the like.

EXAMPLES

Next, the present invention will be described in more detail by showing Examples, however, the present invention is by no means limited to these Examples. Incidentally, in the following Examples, the viable cell count of *Lactobacillus casei* was measured by the following method.

Viable Cell Count of *Lactobacillus Casei*

Dried cells of *Lactobacillus casei* were serially diluted with saline (0.85% NaCl). The diluted solution (1 mL) was mixed and diluted with a BCP-added plate count agar medium, and the cells were cultured at $37°$ C. for 72 hours. Thereafter, formed colonies were counted, and the obtained count was multiplied by the dilution ratio, and the obtained value was used as the viable cell count of *Lactobacillus casei*.

Example 1

Preparation of Dried Cells of *Lactobacillus Casei* (1)

*Lactobacillus casei* YIT 9029 was anaerobically cultured at $37°$ C. for 20 hours in a medium (pH 7) containing yeast extract (1%), monopotassium phosphate (0.1%), dipotassium phosphate (0.2%), and lactose (2%). After completion of culturing, the culture solution was cooled to $20°$ C. or lower, and the pH of the solution was adjusted to 7.0 with a 5 N sodium hydroxide solution. The cells obtained by centrifuging this culture solution (14000 G, $4°$ C., 30 minutes) were collected. A dispersion medium was prepared to a total volume of 1000 mL according to the composition shown in the following Table 1. Then, the cells were suspended in the dispersion medium at $2.0 \times 10^{11}$ cfu/mL. The cell suspension was dispensed in a tray, and dried cells were prepared by a lyophilization method. Incidentally, the lyophilization was performed using a lyophilizer TAKARA FREEZE-DRYER TF20-80 TANNS (TAKARA ATM Ltd.) under the condition of shelf temperature of −40° C. for hours, and thereafter, under the condition of shelf temperature of 20° C. for 80 hours. The obtained dried cells were ground using a mill, and the ground cells were filled in capsules (made of hydroxypropylmethyl cellulose) in an amount of 0.2 g per capsule under a general atmospheric composition without degassing, and then, the capsules were placed in an aluminum pouch along with an oxygen absorber (manufactured by Mitsubishi Gas Chemical Company, Inc.) and stored at 35° C. for 4 weeks, and thereafter, the viable cell count of *Lactobacillus casei* was measured. The ratio of the viable cell count after storage to the viable cell count at the start of storage (survival rate) is shown in Table 1.

TABLE 1

| Components of dispersion medium (%) | | Invention method 1 | Comparative method 1 | Comparative method 2 |
|---|---|---|---|---|
| Protective agent | Na glutamate | 10 | 10 | 10 |
| | Trehalose | 10 | 10 | 10 |
| | Dextrin | — | — | 5 |
| Antioxidant | Na ascorbate | 1 | — | — |
| | Vitamin E | — | — | — |
| | Catechin | — | — | — |
| Chelating agent | Na citrate | 1 | — | — |
| | Purified water | Remainder | Remainder | Remainder |
| Survival rate (%) after storage at 35° C. for 4 weeks | | 33 | 22 | 22 |

The invention method 1 in which the dispersion medium containing the protective agent (sodium glutamate and trehalose), the antioxidant (sodium ascorbate), and the chelating agent (sodium citrate) was used showed a higher survival rate than the comparative method 1 and the comparative method 2 in which the dispersion medium containing no antioxidant or chelating agent was used.

Example 2

Preparation of Dried Cells of *Lactobacillus Casei* (2)

Lyophilized cells of *Lactobacillus casei* YIT 9029 were prepared in the same manner as in Example 1 except that the composition of the dispersion medium was changed as shown in the following Table 2, and filled in capsules (made of hydroxypropylmethyl cellulose) in an amount of 0.2 g per capsule under a general atmospheric composition without degassing, and then, the capsules were placed in an aluminum pouch along with an oxygen absorber (manufactured by Mitsubishi Gas Chemical Company, Inc.) and stored at 35° C. for 4 weeks, and thereafter, the viable cell count of *Lactobacillus casei* was measured. The ratio of the viable cell count after storage to the viable cell count at the start of storage (survival rate) is shown in Table 2.

TABLE 2

| Components of dispersion medium (%) | | Invention method 1 | Comparative method 3 | Comparative method 4 | Comparative method 5 |
|---|---|---|---|---|---|
| Protective agent | Na glutamate | 10 | 10 | 10 | 10 |
| | Trehalose | 10 | 10 | 10 | 10 |
| | Dextrin | — | — | — | — |
| Antioxidant | Na ascorbate | 1 | 1 | — | — |
| | Vitamin E | — | — | 0.85 | — |
| | Catechin | — | — | — | 0.05 |
| Chelating agent | Na citrate | 1 | — | — | — |
| | Purified water | Remainder | Remainder | Remainder | Remainder |
| Survival rate (%) after storage at 35° C. for 4 weeks | | 33 | 27 | 17 | 16 |

The survival rate of the comparative methods 3 to 5 in which the dispersion medium containing no chelating agent was used was lower than that of the invention method 1. From the results of Examples 1 and 2, it was shown that the survival rate after long-term storage at a high temperature of the dried cells produced using the dispersion medium containing the following three components: the protective agent, the antioxidant, and the chelating agent was higher than in the case of using only the protective agent or the case using only the protective agent and the antioxidant.

Example 3

Preparation of Dried Cells of *Lactobacillus Casei* (3)

Lyophilized cells of *Lactobacillus casei* YIT 9029 were prepared in the same manner as the invention method 1 of Example 1, and filled in capsules (made of hydroxypropylmethyl cellulose) in an amount of 0.2 g per capsule under a general atmospheric composition without degassing, and then, the capsules were packaged in PTP (press through package made of an aluminum sheet and vinyl chloride), and the capsules in the package were placed in an aluminum pouch along with an oxygen absorber (manufactured by Mitsubishi Gas Chemical Company, Inc.) and stored under the conditions shown in Table 3, and thereafter, the viable cell count of *Lactobacillus casei* was measured. The ratio of the viable cell count after storage to the viable cell count at the start of storage (survival rate) is shown in Table 3. Incidentally, the storage conditions of 2° C. for 1 day→35° C. for 2 days 30° C. for 6 days→22° C. for 6 months were set on the assumption that the lyophilized cells are transported at 30 to 35° C., and thereafter stored at 22° C. Further, the lyophilized cells after storage had low hygroscopicity and did not form an aggregate, and the appearance, color, and smell were the same as those at the start of storage and favorable.

TABLE 3

| | 2° C. for 1 day → 35° C. for 2 days → 30° C. for 6 days → 22° C. for 6 months | 22° C. for 6 months |
|---|---|---|
| Survival rate (%) | 39 | 41 |

It was shown that the viability was favorable under both the storage conditions of 2° C. for 1 day→35° C. for 2 days→30° C. for 6 days→22° C. for 6 months, and the storage conditions of 22° C. for 6 months, and in particular, it was shown that the viability was favorable even under the storage conditions of 2° C. for 1 day→35° C. for 2 days→30° C. for 6 days→22° C. for 6 months which were set on the assumption of practical use.

INDUSTRIAL APPLICABILITY

The dried microbial cells obtained according to the method of the present invention have a high viable cell survival rate even if the cells are stored at a high temperature for a long period of time. Therefore, the dried microbial cells are extremely excellent from the viewpoints of distribution and storage. Further, the dried microbial cells obtained according to the method of the present invention can be utilized in foods, drinks, etc.

The invention claimed is:

1. A method for producing dried microbial cells, the method comprising:
   suspending microbial cells in a dispersion medium which is an aqueous solution comprising sodium glutamate and trehalose as protective agents, sodium ascorbate as an antioxidant, and sodium citrate as a chelating agent, to obtain a suspension; and then
   drying the suspension.

2. The method for producing dried microbial cells according to claim 1, wherein the dispersion medium comprises:
   from 5 to 30 mass % of the protective agents;
   from 0.05 to 5 mass % of the antioxidant; and
   from 0.5 to 5 mass % of the chelating agent.

3. The method for producing dried microbial cells according to claim 1, wherein the microbial cells are cells of a microorganism belonging to the genus *Lactobacillus*.

4. The method for producing dried microbial cells according to claim 1, wherein the drying is performed by a lyophilization method.

5. The method for producing dried microbial cells according to claim 3, wherein the microbial cells are *Lactobacillus easel*.

6. The method for producing dried microbial cells according to claim 5, wherein the microbial cells are *Lactobacillus casei* YIT 9029.

* * * * *